US010030052B2

(12) United States Patent
Settembre et al.

(10) Patent No.: US 10,030,052 B2
(45) Date of Patent: Jul. 24, 2018

(54) PARVOVIRUS VP1 UNIQUE REGION POLYPEPTIDES AND COMPOSITIONS THEREOF

(75) Inventors: Ethan Settembre, Lexington, MA (US); Sumana Chandramouli, Winchester, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/234,648

(22) PCT Filed: Jul. 25, 2012

(86) PCT No.: PCT/US2012/048200
§ 371 (c)(1), (2), (4) Date: Jan. 24, 2014

(87) PCT Pub. No.: WO2013/016460
PCT Pub. Date: Jan. 31, 2013

(65) Prior Publication Data
US 2014/0170187 A1 Jun. 19, 2014

Related U.S. Application Data

(60) Provisional application No. 61/583,116, filed on Jan. 4, 2012, provisional application No. 61/511,211, filed on Jul. 25, 2011.

(51) Int. Cl.

| | |
|---|---|
| *C07K 14/005* | (2006.01) |
| *A61K 39/23* | (2006.01) |
| *C07K 16/08* | (2006.01) |
| *G01N 33/569* | (2006.01) |
| *A61K 39/12* | (2006.01) |
| *A61K 39/00* | (2006.01) |

(52) U.S. Cl.
CPC ............ *C07K 14/005* (2013.01); *A61K 39/12* (2013.01); *A61K 39/23* (2013.01); *C07K 16/081* (2013.01); *G01N 33/56983* (2013.01); *A61K 2039/5258* (2013.01); *A61K 2039/55566* (2013.01); *C07K 2317/34* (2013.01); *C12N 2750/14222* (2013.01); *C12N 2750/14234* (2013.01); *G01N 2333/015* (2013.01); *G01N 2469/20* (2013.01)

(58) Field of Classification Search
None
See application file for complete search history.

(56) References Cited

FOREIGN PATENT DOCUMENTS

| | | | |
|---|---|---|---|
| WO | WO 2006/032697 | * | 3/2006 |
| WO | WO2006032697 | | 3/2006 |

OTHER PUBLICATIONS

Kapoor et al., The Journal of Infectious Diseases, 2009; 199:196-200.*

Bostic et al., Quantitative analysis of neutralizing immune responses to human parvovirus B19 using a novel reverse transcriptase-polymerase chain reaction-based assay. J Infect Dis. ;179:619-26, 1999.

Kurtzman, GJ, Immune response to B19 parvovirus and an antibody defect in persistent viral infection. J Clin Invest. 84:1114-23. 1989.

Lu, J., Activation of synoviocytes by the secreted phospholipase A2 motif in the VP1-unique region of parvovirus B19 minor capsid protein. J Infect Dis.193:582-90, 2006.

Modrow S and Dorsch S. Antibody responses in parvovirus B19 infected patients. Pathol Biol (Paris). 50:326-31, 2002.

Ozawa, K and Young, N. Characterization of capsid and noncapsid proteins of B19 parvovirus propagated in human erythroid bone marrow cell cultures. J Virol. 61:2627-30, 1987.

Palmer, P., et al., Antibody response to human parvovirus B19 in patients with primary infection by immunoblot assay with recombinant proteins. Clin Diagn Lab Immunol. 3:236-8, 1996.

Saikawa, T. et al., Neutralizing linear epitopes of B19 parvovirus cluster in the VP1 unique and VP1-VP2 junction regions. J Virol. 67:3004-9, 1993.

Young, NS and Brown, KE, Parvovirus B19. N Engl J Med. 350:586-97, 2004.

* cited by examiner

*Primary Examiner* — Nicole Kinsey White
(74) *Attorney, Agent, or Firm* — Virginia G. Campen

(57) ABSTRACT

The present invention is directed to mutant parvovirus VP1 unique region polypeptides, compositions comprising such polypeptides, methods of making such compositions, as well as methods for identifying the likely presence of parvovirus-neutralizing antibodies, and methods for assessing the functional immunogenicity of parvovirus vaccines and measuring a correlate of efficacy to assess a treatment for parvovirus infection.

6 Claims, 5 Drawing Sheets

FIG. 1

```
VP1u region            167 PYTHW 171
                           PY HW
MAB8293 epitope (VP2)  336 PYHHW 340
```

FIG. 2

WT = 167 PYTHW 171
AT = 167 AATAA 171
YT = 167 AYTAA 171

FIG. 4

Sequence alignment for Parvovirus B19 genotypes 1-3

```
Overall score in ClustalW: >90

VP1u_B19_Type1  MSKESGKWWESDDKFAKAVYQQLVEFYEKVTGTDLELIQILKDHYNISLDNPLENPSSLF 60
VP1u_B19_Type2  MSKESGKWWESDDKFAKDVYKQFVEFYEKVTGTDLELIQILKDHYNISLDNPLENPSSLF 60
VP1u_B19_Type3  MSKTTDKWWESSDKFAQDVYKQFVQFYEKATGTDLELIQILKDHYNISLDNPLENPSSLF 60
                *** :.*****.****: **:*:*:****.******************************

VP1u_B19_Type1  DLVARIKNNLKNSPDLYSHHFQSHGQLSDHPHALSSSSSHAEPRGENAVLSSEDLHKPGQ 120
VP1u_B19_Type2  DLVARIKSNLKDSPDLYSHHFQSHGQLSDHPHALSPSSSHTEPRGENAVLSSEDLHKPGQ 120
VP1u_B19_Type3  DLVARIKSNLKNSPDLYSHHFQSHGQLSDHPHALSPSNSSTEPRGENAVLSSEDLHKPGQ 120
                *******.***:***********************.*.* :*******************

VP1u_B19_Type1  VSVQLPGTNYVGPGNELQAGPPQSAVDSAARIHDFRYSQLAKLGINPYTHWTVADEELLK 180
VP1u_B19_Type2  VSIQLPGTNYVGPGYELQAGPPQSAVDSAARIHDFRYSQLAKLGINPYTYWTVADEELLK 180
VP1u_B19_Type3  VSIQLPGTNYVGPGNELQAGPPQNAVDSAARIHDFRYSQLAKLGINPYTHWTVADEELLK 180
                **:*********** ********.*************************:**********

VP1u_B19_Type1  NIKNETGFQAQVVKDYFTLKGAAAPVAHFQGSLPEVPAYNASEKYPS 227
VP1u_B19_Type2  NIKNESGFQAQAVKDYFTLKGAAAPVAHFQGSLPEVPAYNASEKYPS 227
VP1u_B19_Type3  NIKNETGFQAQAVKDYFTLKGAAAPVAHFQGSLPEVPAYNASEKYPS 227
                *****:*****.***********************************
```

FIG. 5
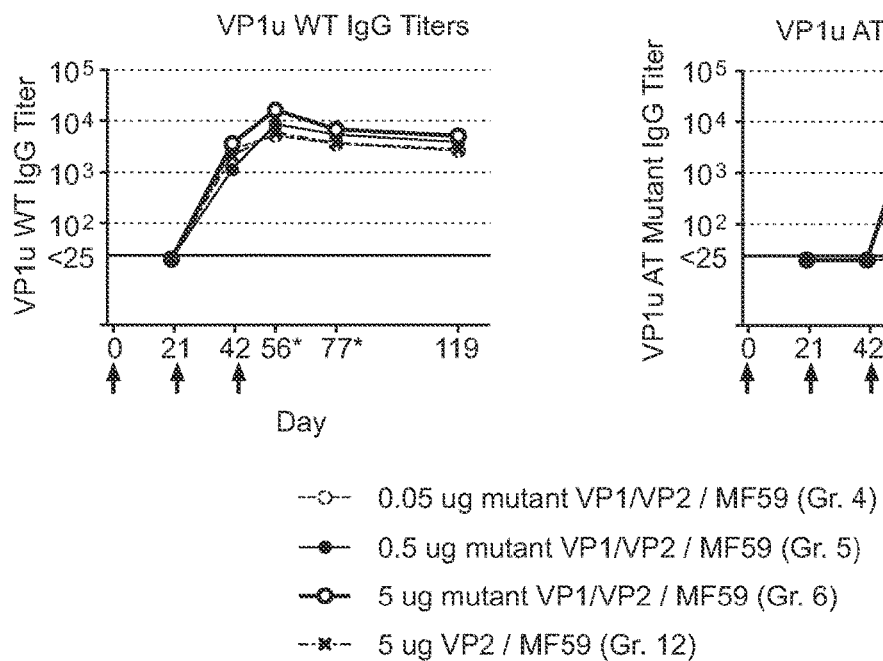
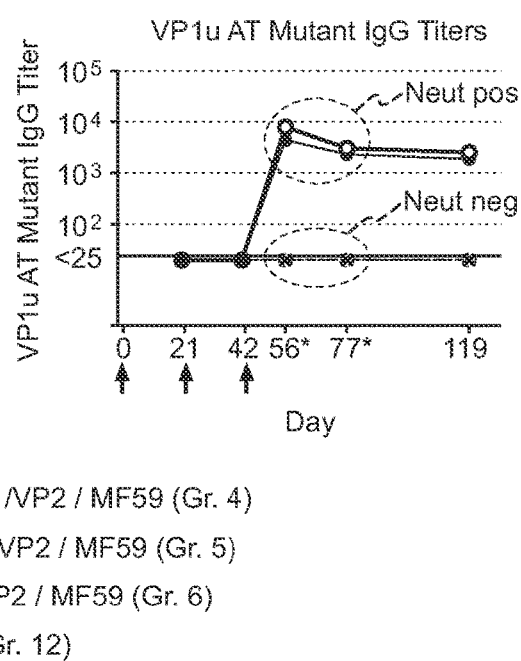
--○-- 0.05 ug mutant VP1/VP2 / MF59 (Gr. 4)
--●-- 0.5 ug mutant VP1/VP2 / MF59 (Gr. 5)
--○-- 5 ug mutant VP1/VP2 / MF59 (Gr. 6)
--✕-- 5 ug VP2 / MF59 (Gr. 12)

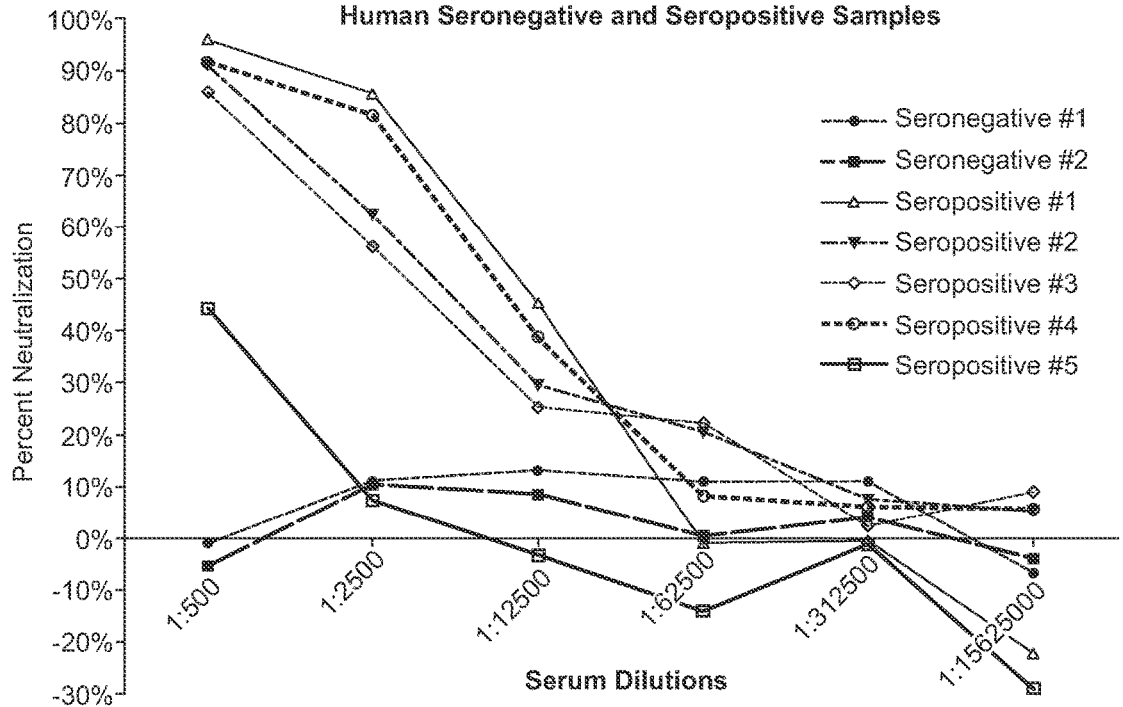

PARVOVIRUS VP1 UNIQUE REGION POLYPEPTIDES AND COMPOSITIONS THEREOF

RELATED APPLICATIONS

This application is the U.S. National Phase of International Application No. PCT/US2012/048200, filed Jul. 25, 2012 and published in English, which claims priority from U.S. Provisional Application No. 61/511,211 filed Jul. 25, 2011 and from U.S. Provisional Application No. 61/583,116 filed Jan. 4, 2012. The teachings of the above applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 303822016800SubSeqList.txt, date recorded: Mar. 8, 2016, size: 10 KB).

FIELD OF THE INVENTION

The present invention relates to the fields of assessing immunogenicity of vaccines and treatments, identifying subjects who may be at risk for viral infection, and determining a correlate of neutralizing activity in antibody preparations. Although not limited to a specific virus, the present invention also relates to the field of parvovirus B19 vaccines and treatments.

BACKGROUND

Members of the Parvoviridae family are non-enveloped icosahedral viruses that contain a single-stranded linear DNA genome. Members of this family infect a variety of vertebrates, including humans, mice, mustelids, skunks, raccoons, cows, canines, primates, and ducks, as well as insects. Parvovirus B19, a member of the genus Erythrovirus, is pathogenic in humans. Parvovirus B19 infection produces mild, self-limiting illness in immunocompetent, hematologically normal individuals; however, it may cause serious illness in individuals with cancer such as leukemia, sickle-cell disease or other types of chronic anemia, those born with immune deficiencies, those who have received an organ transplant, or those who have human immunodeficiency virus (HIV). In such individuals, parvovirus B19 can cause severe anemia, both chronic and acute. Parvovirus B19 infection in pregnant women is also associated with hydrops fetalis due to severe fetal anemia, sometimes leading to miscarriage or stillbirth. The most common presentation of parvovirus B19 is as a childhood exanthem called fifth disease or erythema infectiosum, commonly known as slapped cheek syndrome.

The parvovirus genera that infect vertebrates (Parvovirus, Erythrovirus, Dependovirus, Ambovirus, and Bocavirus) have a viral capsid made of at least two structural proteins, VP1 and VP2. For example, the parvovirus B19 capsid consists of an 83 kDa minor structural protein, VP1, and a 58 kDa major structural protein, VP2, which are found in a ~5% to ~95% ratio (Ozawa et al. J. Virol. 61(8): 2627-30 (1987)). The sequences of the two proteins are co-linear, with VP2 being identical to the carboxyl-terminal region of VP1; however, VP1 comprises an additional 227 amino acids at the amino-terminus, which is known as the VP1 unique region. The capsid proteins for the other members of the parvovirus genera that infect vertebrates have a similar structural relationship, although the VP1 unique region of these other members is generally shorter.

The VP1 unique region of parvovirus B19 is known to contain epitopes recognized by the longest lasting neutralizing antibodies that are raised during natural parvovirus infection (Modrow S and Dorsch S. Pathol Biol (Paris). 50: 326-331 (2002)). Furthermore some experiments with virus-like particles show that neutralizing antibodies are only raised when the VP1 unique region is present (Young N S and Brown K E. NEJM. 350:586-597 (2004)). However, as of yet, no vaccine or practical, long lasting treatment has been developed for infection by parvoviruses that primary infect humans.

Modified VP1 capsids with mutations in the active site for phospholipase $A_2$, located in the unique region, have been described in US2007/0286870. However, as expressly taught in paragraph 11 of this application, these changes are limited to those which do "not significantly alter the immunological performance of the vaccine (i.e., in that the immunogenic properties should not be adversely affected by the mutation)."

Human immunoglobulin-containing preparations are sometimes used to treat chronic parvovirus B19 infections in immunodeficient individuals. However, immunoglobulin injections are not sufficiently practical, long lasting, or affordable for widespread or routine prophylactic use. Excluding those with fifth disease from social interaction, e.g., at work, child care centers, or schools, is not an effective way to prevent the spread of the virus, because individuals are contagious well before they develop the signatory rash. Furthermore, not all such immunoglobulin-containing preparations (IV-Ig) are effective since they may not contain antibodies capable of neutralizing parvovirus B19. Current tests of IV-Ig lots do not discriminate between the presence of non-neutralizing and neutralizing antibody against parvovirus B19. This creates uncertainty about the potency of a lot of IV-Ig for treatment of parvovirus B19 infections. Uncertainty about anti-viral potency could result in an insufficient dose being given, necessitating multiple injections for treatment of infection or could result in a patient receiving more IV-Ig than is needed for treatment. Thus there is a need for improved methods for estimating the level of neutralizing antibody to assure that a patient is treated with an appropriate amount of IV-IG.

Further, despite what is known in the art, there remains a need for development of parvovirus vaccines and treatments, and methods of identifying individuals who may be at risk for infection. Current development and use after development of parvovirus B19 vaccines and treatments is hampered by the lack of an inexpensive, simple, and rapid means of measuring a correlate of protection. The knowledge of human and animal parvovirus infections continues to advance, as indicated by the recent discovery of human bocavirus as a disease-causing agent. Thus, the need for the development of related vaccines and serologic assays against other parvoviruses is anticipated. One of skill in the art can readily apply the teachings of this disclosure to other parvoviruses as they are discovered. Presently, the ability of a parvovirus B19 vaccine to elicit functional antibodies against the virus and the potency of therapeutic candidates can only be assessed by directly detecting neutralization of viral infection using cell-based assays which are expensive, complicated, cumbersome, and time-consuming as they require the use of reagents such as erythroid progenitor cells which must be cultured before they can be used in the assay.

Such assays also display high variability of results (Wong et al. J. Clin. Virol. 35: 407-413 (2007)). Thus, there also exists a need for improved methods for assessing the functional antibody titers elicited by of such vaccines to allow effective development of such vaccines and then effective use after having been developed.

SUMMARY OF THE INVENTION

The present invention addresses these needs by providing mutant parvovirus VP1 unique region polypeptides which can be used to determine whether an antibody preparation is likely to contain parvovirus-neutralizing antibodies, compositions comprising such polypeptides, and methods of making such compositions. These polypeptides can also be used to elicit parvovirus-neutralizing antibodies. The present invention also provides methods which make use of the ability of these mutant parvovirus VP1 unique region polypeptides to determine whether an antibody preparation is likely to contain parvovirus-neutralizing antibodies, for example, methods to assess functional immunogenicity of parvovirus vaccines and to measure a correlate of efficacy for a treatment of parvovirus infection.

One aspect of the invention is a polypeptide having a mutant parvovirus VP1 unique region wherein an epitope for non-neutralizing parvovirus antibodies has been mutated to alter its antigenic properties. Another aspect of the invention is a polypeptide having a mutant parvovirus VP1 unique region wherein an epitope cross-reactive with antibodies that bind parvovirus VP2 has been mutated to reduce the cross-reactivity. Still another aspect of the invention is a polypeptide having a mutant parvovirus VP1 unique region wherein an epitope including the sequence extending from the amino acid that aligns with amino acid 167 of parvovirus B19 VP1 to the amino acid that aligns with amino acid 171 of parvovirus B19 VP1 has been mutated to alter its antigenic properties.

In certain embodiments of the above aspects where an epitope for non-neutralizing parvovirus antibodies or an epitope including the sequence extending from the amino acid that aligns with amino acid 167 of parvovirus B19 VP1 to the amino acid that aligns with amino acid 171 of parvovirus B19 VP1 has been mutated, the epitope may not cross-react with antibodies that bind parvovirus VP2.

In certain embodiments of the above aspects where an epitope for non-neutralizing parvovirus antibodies or an epitope cross-reactive with antibodies that bind parvovirus VP2 has been inactivated, the epitope may include the sequence extending from the amino acid which aligns with amino acid 167 of parvovirus B19 VP1 to the amino acid which aligns with amino acid 171 of parvovirus B19 VP1.

In certain embodiments of any of the preceding aspects and embodiments, the polypeptide may be isolated or substantially purified or recombinant.

In other embodiments of any of the preceding aspects and embodiments, the epitope has at least one mutation, at least two mutations, at least three mutations, at least four mutations, or at least five mutations.

In still other embodiments of any of the preceding aspects and embodiments, the epitope has at least one mutation. This epitope may have at least one mutation at the amino acid which aligns with amino acid 171 of parvovirus B19 VP1.

In still other embodiments of any of the preceding aspects and embodiments, the epitope has at least two mutations. This epitope may have at least a mutation at the amino acid which aligns with amino acid 170 of parvovirus B19 VP1 and a mutation at the amino acid which aligns with amino acid 171 of parvovirus B19 VP1.

In still other embodiments of any of the preceding aspects and embodiments, the epitope has at least three mutations. The epitope may have at least a mutation at the amino acid which aligns with amino acid 167 of parvovirus B19 VP1, a mutation at the amino acid which aligns with amino acid 170 of parvovirus B19 VP1, and a mutation at the amino acid which aligns with amino acid 171 of parvovirus B19 VP1.

In embodiments of any of the preceding embodiments having a mutation, the mutation may be a deletion. In embodiments of any of the preceding embodiments where the epitope has a mutation, the mutation may be a deletion. In still other embodiments of any of the preceding embodiments where the epitope has a mutation, the mutation may be a substitution. In other embodiments of any of the preceding embodiments where the epitope has a mutation, the mutation may be an insertion. In other embodiments of any of the preceding embodiments where the epitope has a mutation, which in certain embodiments of any of the preceding embodiments is not a Y168F mutation or a H170Y mutation or a W171L.

In any of the preceding aspects and embodiments, the mutant parvovirus VP1 unique region may have 70% identity to SEQ ID NO: 1, 80% identity to SEQ ID NO: 1, 90% identity to SEQ ID NO: 1, or 95% identity to SEQ ID NO: 1, 97% identity to SEQ ID NO: 1, 98% identity to SEQ ID NO: 1, or 99% identity to SEQ ID NO: 1. In any of the preceding aspects and embodiments, the mutant parvovirus VP1 unique region may have 70% identity to SEQ ID NO: 4, 80% identity to SEQ ID NO: 4, 90% identity to SEQ ID NO: 4, or 95% identity to SEQ ID NO: 4, 97% identity to SEQ ID NO: 4, 98% identity to SEQ ID NO: 4, or 99% identity to SEQ ID NO: 4. In any of the preceding aspects and embodiments, the mutant parvovirus VP1 unique region may have 70% identity to SEQ ID NO: 5, 80% identity to SEQ ID NO: 5, 90% identity to SEQ ID NO: 5, or 95% identity to SEQ ID NO: 5, 97% identity to SEQ ID NO: 5, 98% identity to SEQ ID NO: 5, or 99% identity to SEQ ID NO: 5. In any of the preceding aspects and embodiments, the mutant parvovirus VP1 unique region may have 70% identity to SEQ ID NO: 6, 80% identity to SEQ ID NO: 6, 90% identity to SEQ ID NO: 6, or 95% identity to SEQ ID NO: 6, 97% identity to SEQ ID NO: 6, 98% identity to SEQ ID NO: 6, or 99% identity to SEQ ID NO: 6.

In any of the preceding aspects and embodiments, the parvovirus may be a member of the Erythrovirus, Dependovirus, or Bocavirus genera. In a preferred embodiment, the parvovirus is B19 in any of the preceding aspects and embodiments.

Another aspect of the invention is an immunogenic composition that includes the polypeptide of any of the above aspects and embodiments, and a pharmaceutically acceptable carrier.

Still another aspect of the invention is a polynucleotide encoding the any of the above aspects and embodiments of polypeptides of the invention.

Still another aspect is a vaccine that includes the immunogenic compositions or polynucleotides described in the above aspects. In some embodiments, the vaccine further includes an adjuvant, for example, a submicron emulsion comprising squalene and polysorbate 80. A related aspect of the invention is method of raising an immune response to parvovirus in a subject by administering the immunogenic compositions, polynucleotides, or vaccines of the preceding aspects and embodiments.

Another aspect is a host cell that includes a plasmid encoding the any of the polypeptides of any of the above aspects and embodiments relating to polypeptides. A related aspect is a method of production of a polypeptide by providing a host cell that includes the polynucleotide of the above aspect operatively linked to a promoter operable under conditions whereby the encoded polypeptide is expressed; and recovering the polypeptide from the host cell.

An aspect of the invention is a method of assessing the functional immunogenicity of a parvovirus vaccine component by providing an antibody preparation from a subject inoculated with a parvovirus vaccine component; contacting the antibody preparation with the polypeptide of any of the above aspects and embodiments relating to polypeptides; and assessing functional immunogenicity of a parvovirus vaccine component by detecting whether the antibody preparation binds to the polypeptide. In some embodiments, the parvovirus vaccine component is a protein, a proteoglycan, a lipoprotein, an outer membrane vesicle, a virus-like particle, or an entire virus. In a preferred embodiment, the parvovirus vaccine component includes an polypeptide of any of the preceding aspects and embodiments.

Another aspect of the invention is a method of identifying subjects who may be at risk for parvovirus infection by providing an antibody preparation from a subject who may be at risk for parvovirus infection; contacting the antibody preparation with the polypeptide of any of the above aspects and embodiments relating to polypeptides; and identifying subjects who may be at risk for parvovirus infection by detecting whether the antibody preparation binds to the polypeptide. In some embodiments, the subject may be at risk for infection because the subject may have been exposed to parvovirus or may have been in an environment likely to contain parvovirus.

Still another aspect of the invention is a method for determining whether an antibody preparation is likely to contain neutralizing parvovirus antibodies by providing an antibody preparation; contacting the antibody preparation with the polypeptide of any of the above aspects and embodiments relating to polypeptides; and determining whether the antibody preparation is likely to contain neutralizing parvovirus antibodies by detecting whether the antibody preparation binds to the polypeptide. In some embodiments, the antibody preparation is immune globulins.

Yet another aspect of the invention is a method for determining potency of an antibody preparation against parvovirus by providing an antibody preparation; contacting the antibody preparation with the polypeptide of any of the above aspects and embodiments relating to polypeptides; and assessing potency by detecting whether the antibody preparation binds to the polypeptide. In some embodiments, the antibody preparation is immune globulin. In some embodiments which may be combined with the preceding embodiments, the method includes a further step of adjusting a dose of the antibody preparation using the assessed potency.

Another aspect of the invention is a method of measuring a correlate of efficacy to assess a prophylactic or a treatment for parvovirus infection by providing an antibody preparation from a subject having received the prophylactic or the treatment for parvovirus infection; contacting the antibody preparation with the polypeptide of any of the above aspects and embodiments relating to polypeptides; and measuring a correlate of efficacy to assess the prophylactic or the treatment for parvovirus infection by detecting whether the antibody preparation binds to the polypeptide. In some embodiments, the treatment for parvovirus infection is administration of immune globulins. In some other embodiments, the prophylactic for parvovirus infection is administration of a parvovirus vaccine.

Yet another aspect of the invention is a method of measuring a correlate of neutralization activity to assess a prophylactic or a treatment for parvovirus infection by providing an antibody preparation from a subject having received the prophylactic or the treatment for parvovirus infection; contacting the antibody preparation with the polypeptide of any of the above aspects and embodiments relating to polypeptides; and measuring a correlate of neutralization activity to assess the prophylactic or the treatment for parvovirus infection by detecting whether the antibody preparation binds to the polypeptide. In some embodiments, the treatment for parvovirus infection is administration of immune globulins. In some other embodiments, the prophylactic for parvovirus infection is administration of a parvovirus vaccine.

Still another aspect of the invention is a method of measuring a correlate of protection to assess a prophylactic or a treatment for parvovirus infection by providing an antibody preparation from a subject having received the prophylactic or the treatment for parvovirus infection; contacting the antibody preparation with the polypeptide of any of the above aspects and embodiments relating to polypeptides; and measuring a correlate of protection to assess the prophylactic or the treatment for parvovirus infection by detecting whether the antibody preparation binds to the polypeptide. In some embodiments, the treatment for parvovirus infection is administration of immune globulins. In some other embodiments, the prophylactic for parvovirus infection is administration of a parvovirus vaccine.

Yet another aspect of the invention is a method of measuring a correlate of immunoprophylactic or immunotherapeutic potency to assess a prophylactic or a treatment for parvovirus infection by providing an antibody preparation from a subject having received the prophylactic or the treatment for parvovirus infection; contacting the antibody preparation with the polypeptide of any of the above aspects and embodiments relating to polypeptides; and measuring the immunoprophylactic or immunotherapeutic potency to assess the prophylactic or the treatment for parvovirus infection by detecting whether the antibody preparation binds to the polypeptide. In some embodiments, the treatment for parvovirus infection is administration of immune globulins. In some other embodiments, the prophylactic for parvovirus infection is administration of a parvovirus vaccine.

In any of the preceding aspects and embodiments relating to methods, the step of detecting may be performed with an ELISA assay, a radio-immunoassay, a fluorometric immunoassay, or latex agglutination assay. In a preferred embodiment, the detecting is performed with an ELISA assay. The enzyme of the ELISA assay may be horse-radish peroxidase, alkaline phosphatase, β-galactosidase, luciferase, or acetylcholinesterase. The ELISA assay may use a chromogenic, radiolabeled or a fluorescent substrate.

In other embodiments the antibody preparation in any of the preceding aspects and embodiments relating to methods may be a serum sample comprising polyclonal antibodies, polyclonal antibodies, antigen-purified polyclonal antibodies, or a combination of two or more of the foregoing.

Another aspect of the invention is a kit for practicing any of the methods of the invention.

DESCRIPTION OF THE DRAWINGS

FIG. 1 shows the BLAST results for a portion of the epitope for MAB8293(PYHHW (SEQ ID NO: 8)), an antibody to parvovirus B19 VP2, with the parvovirus B19 VP1u sequence (PYTHW (SEQ ID NO: 7)).

FIG. 2 is a Coomassie-stained SDS-PAGE of soluble, purified wild type and mutant VP1u constructs. The wild-type (PYTHW (SEQ ID NO: 7)) and the two mutants (AATAA (SEQ ID NO: 9)) and AYTAA (SEQ ID NO: 10)) have a similar level of purity.

FIG. 4 shows an alignment of the VP1 unique region from the three genotypes of B19 parvovirus: type 1 (SEQ ID NO: 4); type 2 (SEQ ID NO: 5); and type 3 (SEQ ID NO: 6). The cross-reactive epitope is shown in bold with a box around the region.

FIG. 5 shows two graphs of the ELISA titers (y-axis) of sera taken at five time points (x-axis) for four groups (brown, open circles—Group 4 (0.05 µg mutant VP1NP2/MF59); orange, open circles—Group 5 (0.5 µg mutant VP1NP2/MF59); dark-red, open circles—Group 6 (5 µg mutant VP1NP2/MF59); dark-red Xs—Group 12 (5 µg VP2/MF59)). FIG. 5(A) shows the graph of the ELISA titers using VP1u (wt) (y-axis) of sera taken at five time points (x-axis) for four groups. FIG. 5(B) shows the graph of the ELISA titers using VP1u (mt) (y-axis) of sera taken at five time points (x-axis) for four groups.

FIG. 6 shows a graph of the percent neutralization (y-axis) of serial dilutions (x-axis) of two seronegative sera (red circles and orange squares) and five seropositive sera (yellow triangle, green, upside-down triangles, blue diamonds, purple open circles, and pink open squares).

DESCRIPTION OF THE TABLES

Figure 3:
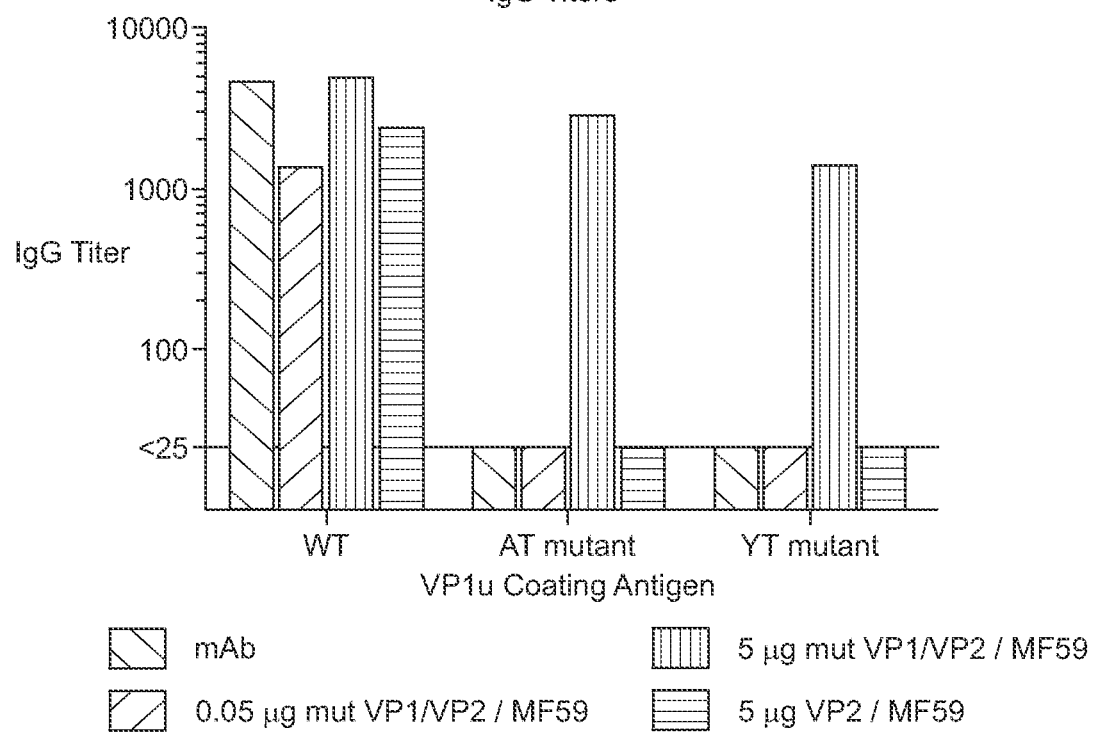
FIG. 3 shows ELISA titers using the WT protein and mutant VP1 constructs as the coating antigen. Pooled sera from mice that have been immunized with different parvovirus B19 vaccines at the 5 weeks post the $3^{rd}$ immunization time point were tested. In the key, "mAb" refers to a MAB8293 control, "VP1/VP2" and "VP2" refer to the composition of the immunizing VLPs, and "MF59" indicates the use of the adjuvant in the immunizations.

Table 1 shows the correlation, or lack thereof, between the ELISA results and neutralizing activity for the different VP1 unique region constructs.

Table 2 shows the correlation between the magnitude of the ELISA results and strength of the neutralizing activity for the different VP1 unique region constructs.

DETAILED DESCRIPTION OF THE PREFERRED EMBODIMENTS

I. Overview

The present invention relates to mutant parvovirus VP1 unique region polypeptides wherein an epitope for non-neutralizing parvovirus antibodies has been mutated to alter its antigenic properties, related compositions, and methods of using such polypeptides. In certain embodiments, the mutant parvovirus VP1 unique region does not bind antibodies that cross-react with parvovirus VP2.

Early reports in the literature have suggested that the measurement of antibody binding to the VP1 unique region would be useful for identifying and measuring neutralizing antibodies in sera (Kurtzman, G J et al. J. Clin. Inv. 84:1114-1123, (1989), (Palmer P. Clin. Diagn. Lab. Immunol. (3): 236-238 (1996)). Previous studies demonstrated that the VP1 region of parvovirus B19 contains epitopes to the longest lasting neutralizing antibodies that are raised during natural infection (Modrow S and Dorsch S. Pathol Biol (Paris). 50: 326-331 (2002)) and further, that synthetic peptides from the VP1 unique region elicit antibodies with strong neutralizing ability (Saikawa et al. J. Virol. 67: 3004-3009 (1993)). However, more recent studies have found unexpectedly that there is no correlation between parvovirus B19 neutralization ability and antibody binding to the VP1 unique region (Bostic et al. J. Infect. Dis. 179:619-626 (1999)).

The present invention is based on Applicants' surprising discovery that there is a cross-reactive epitope between VP2 and the VP1 unique region (FIG. 1). Applicants made this discovery when testing sera raised by immunization with a VLP containing VP2 alone. The antibodies in such sera were both non-neutralizing at the level present in the sera and able to bind to the wildtype but not to the mutant VP1 unique region polypeptide. Without wishing to be bound by theory, Applicants believe that this epitope is likely involved in the binding of primarily non-neutralizing antibodies in sera. The binding of antibodies to this epitope is what may have contributed to the signal in previous assays shown in the art that lead to a lack of correlation between a sera sample binding to the VP1 unique region and neutralizing parvovirus B19 in cell-based assays. Applicants have further demonstrated that alteration of this epitope results in a mutant VP1 unique region polypeptide to which antibody binding correlates with parvovirus B19 neutralization ability. It should be understood, while there appears to be a relation between the binding of non-neutralizing antibodies and VP2 cross-reactivity of the epitope described herein, that the present invention is not limited to mutant VP1 unique region polypeptides which do not cross-react with antibodies that bind VP2.

II. Definitions

As used herein, the term "parvovirus" is used to refer to members of the family Parvoviridae which are pathogenic to vertebrates, including Parvovirus, Erythrovirus, Dependovirus, Ambovirus, and Bocavirus.

The term "epitope for non-neutralizing antibodies" refers to an epitope that primarily binds, or preferentially elicits, non-neutralizing antibodies. For example, an epitope is considered to be an "epitope for non-neutralizing antibodies" even if the epitope also binds a small population of neutralizing antibodies.

As used herein, the term "the sequence extending from the amino acid which aligns with amino acid X to the amino acid which aligns with amino acid Y" encompasses amino acid X, amino acid Y, and any of the amino acids between X and Y in the polypeptide sequence which includes amino acids X and Y. An epitope including such a sequence may also encompass flanking sequence on either end.

For purposes of this disclosure, whether an antibody is "neutralizing" or has "neutralization activity" refers to whether the antibody is capable of preventing infection in cell culture.

"Functional immunogenicity" refers to whether a vaccine is capable of eliciting antibodies that neutralize virus in cell culture or is capable of eliciting an immune response that protects animals or humans from disease.

A "correlate of efficacy" for a treatment or a prophylactic, such as a vaccine or antibody preparation, is a parameter that correlates with the efficacy of a treatment, or prophylactic as defined below. For example, whether a vaccine elicits antibodies that are neutralizing is a "correlate of efficacy" for that vaccine if it can be shown that there is a positive association between the presence of or titer of such neutralizing antibodies and prevention or amelioration of disease by that vaccine.

A "correlate of neutralization" for a parvovirus treatment or a prophylactic, such as a vaccine or antibody preparation, is a parameter that correlates with neutralization of parvovirus infection in a cell based assay without actually requiring testing or assaying for neutralization to measure or determine the parameter.

A "correlate of protection" for a prophylactic, such as a vaccine or antibody preparation, is a parameter that correlates with the ability of the prophylactic to protect a subject against infection, disease or death.

A "correlate of potency" for a treatment or a prophylactic, such as a vaccine or antibody preparation is a parameter that correlates with the dose of the treatment of prophylactic required for a clinical effect.

As used herein, "efficacy" of a vaccine component refers to whether the vaccine component prevents infection, or reduces the severity or duration of clinical symptoms or signs of infection in a subject having been inoculated with the vaccine component or in the fetus or newborn born to a woman inoculated with the vaccine component, or reduces the transmission of the disease to other individuals. Similarly, "efficacy" of a treatment refers to whether the treatment is capable of reducing the severity of, reducing the duration of, completely suppressing the clinical symptoms of infection, or eliminating the infection entirely, or reducing the transmission of the disease to other individuals.

III. Mutant Parvovirus VP1 Unique Region Polypeptides

The mutant parvovirus VP1 unique region polypeptides described above can be derived from any parvovirus that infects vertebrates, but are preferably derived from a genus that infects humans, i.e., Erythrovirus, Dependovirus, or Bocavirus. In a preferred embodiment, the parvovirus is the species B19 from the genus Erythrovirus. In another embodiment, the parvovirus is human parvovirus 4.

Accordingly, given the diversity of different parvoviruses, as would be readily understood by one of skill in the art, the exact position of the mutation in the non-neutralizing epitope within the parvovirus VP1 unique region will depend on the particular sequence of the wild-type VP1 unique region, which will differ depending on the specific genus and possibly even depending on the particular parvovirus strain within the genus. Thus the mutations sufficient to alter the antigenic properties for the epitope for non-neutralizing parvovirus antibodies are not in a fixed amino acid position, but rather at the amino acid which aligns with a particular amino acid of parvovirus B19 VP1.

Amino acids that align and percent identity can be determined using a pairwise alignment algorithm, each moving window of x amino acids from N terminus to C terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer.

The preferred pairwise alignment algorithm is the Needleman-Wunsch global alignment algorithm (3), using default parameters (e.g., with Gap opening penalty=10.0, and with Gap extension penalty=0.5, using the EBLOSUM62 scoring matrix). This algorithm is conveniently implemented in the needle tool in the EMBOSS package.

The mutations can be any type of mutation which successfully destroys the epitope for non-neutralizing parvovirus antibodies. Typically, the mutation is within the region extending from the amino acid which aligns with amino acid 167 of parvovirus B19 VP1 to the amino acid which aligns with amino acid 171 of parvovirus B19 VP1. Isolates of parvovirus B19 show some natural degree of variation in this region. For example, one isolate has a tyrosine residue at amino acid 170 rather than a histidine residue. Another isolate has a leucine residue as amino acid 171 rather than a tryptophan residue. Some embodiments exclude such naturally occurring variation in this region.

The epitope may contain at least one, at least two, at least three, at least four, or at least five mutations. In some embodiments, the epitope within the mutant parvovirus VP1 unique region polypeptide has least three mutations including a mutation at the amino acid which aligns with amino acid 167 of parvovirus B19 VP1, a mutation at the amino acid which aligns with amino acid 170 of parvovirus B19 VP1, and a mutation at the amino acid which aligns with amino acid 171 of parvovirus B19 VP1. In other embodiments, the epitope has at least two mutations including a mutation at the amino acid which aligns with amino acid 170 of parvovirus B19 VP1 and a mutation at the amino acid which aligns with amino acid 171 of parvovirus B19 VP1. In still other embodiments, the epitope has at least one mutation at the amino acid which aligns with amino acid 171 of parvovirus B19 VP1.

In preferred embodiments, the epitope within a mutant parvovirus VP1 B19 unique region polypeptide has least three mutations including a mutation at amino acid 167 of parvovirus B19 VP1, amino acid 170 of parvovirus B19 VP1, and amino acid 171 of parvovirus B19 VP1.

Most commonly, the mutations will be deletions, insertions, or substitutions, which may be at separated or contiguous positions within the specified region. Commonly, the substitutions are non-conservative substitutions (i.e., substitutions of one amino acid with another with an unrelated side chain). Genetically encoded amino acids are generally divided into four families: (1) acidic, i.e., aspartate, glutamate; (2) basic, i.e., lysine, arginine, histidine; (3) non-polar, i.e., alanine, valine, leucine, isoleucine, proline, phenylalanine, methionine, tryptophan; and (4) uncharged polar, i.e., glycine, asparagine, glutamine, cysteine, serine, threonine, and tyrosine. Phenylalanine, tryptophan, and tyrosine are sometimes classified jointly as aromatic amino acids. In general, substitution of single amino acids within these families does not have a major effect on the biological activity and therefore may not be sufficient to eliminate binding to the epitope as a single mutation (though the effect of any mutation can be assayed by simple ELISA).

The mutant parvovirus VP1 unique region polypeptides described above have at least 70% identity (e.g., 75%, 80%, 85%, 87.5%, 90%, 91%, 92%, 93%, 94%, 95%, 96%, 97%, 98%, 99%, 99.5% or more) to the corresponding wild-type sequence of the VP1 unique region polypeptide. For example, when the mutant VP1 unique region polypeptide is derived from a B19 polypeptide, the reference sequence is SEQ ID NO: 1.

Other mutant parvovirus VP1 unique region polypeptides comprise at least n consecutive amino acids from corresponding wild-type sequence of the VP1 unique region wherein n is 7 or more (e.g., 8, 10, 12, 14, 16, 18, 20, 25, 30, 35, 40, 50, 60, 70, 80, 90, 100, 150, 200, or more). Other preferred fragments lack one or more amino acids (e.g., 1, 2, 3, 4, 5, 6, 7, 8, 9, 10, 15, 20, 25 or more) from the C-terminus and/or the N-terminus of the corresponding wild-type sequence of the VP1 unique region. Such fragments will include the epitope for non-neutralizing parvovirus antibodies which has been mutated to alter its antigenic properties and at least one neutralizing parvovirus epitope. In certain embodiments, the mutant parvovirus VP1 unique region polypeptides described herein lack at least 70%, at least 80%, at least 90%, at least 95%, at least 97%, at least 98%, at least 99%, or all of the C-terminal sequence of VP1 which is in common with VP2.

Polypeptide Forms

The mutant parvovirus VP1 unique region polypeptides described herein can take various forms (e.g., native, fusions, glycosylated, non-glycosylated, lipidated, non-lipidated, phosphorylated, non-phosphorylated, myristoylated, non-myristoylated, monomeric, multimeric, particulate, denatured, etc.).

Mutant parvovirus VP1 unique region polypeptides described herein may be provided in isolated form (e.g., in a non-naturally occurring context such as substantially purified or recombinantly expressed). Mutant parvovirus VP1 unique region polypeptides described herein may be provided in purified or substantially purified form, i.e., substantially free from other polypeptides (e.g., free from naturally-occurring polypeptides), particularly from other *E. coli* or host cell polypeptides, and are generally at least about 50% pure (by weight), and usually at least about 90% pure, i.e., less than about 50%, and more preferably less than about 10% (e.g., 5%) of a composition is made up of other expressed polypeptides. Thus the purified polypeptides in the compositions are separated from the whole organism in which the molecule is expressed.

Polypeptides are amino acid polymers of any length. The polymer may be linear or branched, it may comprise modified amino acids, and it may be interrupted by non amino acids. The amino acid polymer can also be modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

The invention provides mutant parvovirus VP1 unique region polypeptides comprising a sequence -P-L-Q- or -Q-L-P-, wherein: -P- is a mutant parvovirus VP1 unique region amino acid sequence as defined above, -L- is an optional linker, and -Q- is not a sequence as defined above. Where the N terminus codon of -P- is not ATG, but this codon is not present at the N-terminus of a polypeptide, it will be translated as the standard amino acid for that codon rather than as a Met. Where this codon is at the N terminus of a polypeptide, however, it will be translated as Met. Examples of -Q- moieties include, but are not limited to, histidine tags (i.e., His where n=3, 4, 5, 6, 7, 8, 9, 10 or more), a maltose-binding protein, or glutathione-S-transferase (GST).

IV. Compositions Related to Mutant Parvovirus VP1 Unique Region Polypeptides, Methods of Making, and Methods of Use Production of Polypeptides The mutant parvovirus VP1 unique region polypeptides described herein can be prepared by various means (e.g., recombinant expression, purification from cell culture, chemical synthesis, etc.). Recombinantly expressed proteins are preferred. In one embodiment the invention provides methods of making the mutant parvovirus VP1 unique region polypeptides by providing a host cell containing a polynucleotide operatively linked to a promoter operable under conditions by which the encoded polypeptide is expressed, and recovering the polypeptide from the host cell, e.g., by purifying it from culture supernatants.

The invention also provides host cells containing a plasmid that encodes the mutant parvovirus VP1 unique region polypeptides described herein. The plasmid may include a gene encoding a marker, etc. Preferred host cell are those that produce a mutant parvovirus VP1 unique region polypeptide at the highest yield and with a posttranslational modification profile which induces a subject inoculated with a vaccine containing the polypeptide to produce the greatest number of parvovirus-neutralizing antibodies.

Additionally, the invention provides polynucleotides that encode the mutant parvovirus VP1 unique region polypeptides described herein. Polynucleotides may be prepared in many ways, e.g., by chemical synthesis (e.g., phosphoramidite synthesis of DNA) in whole or in part, by digesting longer nucleic acids using nucleases (e.g., restriction enzymes), by joining shorter nucleic acids or nucleotides (e.g., using ligases or polymerases), from genomic or cDNA libraries, etc.

Polynucleotides are a polymeric form of nucleotides of any length, such as deoxyribonucleotides, ribonucleotides, and/or their analogs. Exemplary polynucleotides include DNA, RNA, DNA/RNA hybrids and DNA or RNA analogs, such as those containing modified backbones (e.g., peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Polynucleotides of the invention may be part of a vector, i.e., part of a nucleic acid construct designed for transduction/transfection of one or more cell types. Vectors may be, for example, cloning vectors which are designed for isolation, propagation and replication of inserted nucleotides, expression vectors which are designed for expression of a nucleotide sequence in a host cell, viral vectors which are designed to result in the production of a recombinant virus or virus-like particle, or shuttle vectors, which comprise the attributes of more than one type of vector.

Immunogenic Compositions

The mutant parvovirus VP1 unique region polypeptides disclosed herein and the polynucleotides that encode them may be useful as active ingredients (immunogens) in immunogenic compositions. As described above, Applicants have discovered that there is an epitope for non-neutralizing parvovirus antibodies within the VP1 unique region and that altering the antigenic properties of this epitope results in a mutant VP1 unique region polypeptide where antibody binding to the polypeptide correlates with parvovirus neutralization ability. Thus the invention may provide alternative immunogenic compositions optimized to elicit neutralizing antibodies.

Immunogenic compositions will usually include components in addition to the antigens, e.g., they typically include one or more pharmaceutically acceptable carrier(s), excipient(s) and/or adjuvant(s).

Pharmaceutically Acceptable Excipients and Carriers

The immunogenic compositions generally include one or more "pharmaceutically acceptable excipients or vehicles" such as water, saline, glycerol, ethanol, and the like singly or in combination Immunogenic compositions will typically, in addition to the components mentioned above, comprise one or more "pharmaceutically acceptable carriers." These include any carrier which does not itself elicit the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. Additionally, an auxiliary substance, such as a wetting or emulsifying agent, pH buffering substance, and the like, may be present. A thorough discussion of pharmaceutically acceptable components is available in Gennaro (2000) Remington: *The Science and Practice of Pharmacy*. 20th Ed., ISBN: 0683306472.

Pharmaceutically acceptable salts can also be used in immunogenic compositions of the invention, for example, mineral salts such as hydrochlorides, hydrobromides, phosphates, or sulfates, as well as salts of organic acids such as acetates, proprionates, malonates, or benzoates.

If desired, antigens can be adsorbed to, entrapped within or otherwise associated with liposomes and particulate carriers such as poly(D,L-lactide co-glycolide) (PLG) microparticles or nanoparticles. Antigens can be conjugated to a carrier protein in order to enhance immunogenicity. See Ramsay et al. (2001) Lancet 357(9251):195-196; Lindberg (1999) Vaccine 17 Suppl 2:S28-36; Buttery & Moxon (2000) J R Coll Physicians Lond 34:163-168; Ahmad & Chapnick (1999) Infect Dis Clin North Am 13:113-133, vii; Goldblatt (1998) J. Med. Microbiol. 47:563-567; European patent 0 477 508; U.S. Pat. No. 5,306,492; WO98/42721; Conjugate Vaccines (eds. Cruse et al.) ISBN 3805549326, particularly vol. 10:48-114; Hermanson (1996) Bioconjugate Techniques ISBN: 0123423368 or 012342335X.

Adjuvants

Immunogenic compositions of the present invention may be administered in conjunction with other immunoregulatory agents. For example, an immunogenic composition of the invention can include an adjuvant. Thorough discussions of vaccine adjuvants are available in *Vaccine Design: The Subunit and Adjuvant Approach* (eds. Powell & Newman) Plenum Press 1995 (ISBN 0-306-44867-X) and *Vaccine Adjuvants: Preparation Methods and Research Protocols* (Volume 42 of Methods in Molecular Medicine series). ISBN: 1-59259-083-7. Ed. O'Hagan. Preferred adjuvants include, but are not limited to, one or more of the following types of adjuvants described below Immunogenic compositions of the present invention may also be pre-mixed with an adjuvant before administration.

Alum

In one embodiment, the adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Retinoic Acid

In one embodiment, the adjuvant for use in the present invention is retinoic acid, the oxidized form of Vitamin A, with only partial vitamin A function.

MF59C.1

In one embodiment, the adjuvant for use in the present invention is MF59C.1, an oil-in-water emulsion (squalene) in citrate buffer. MF59C.1 has been shown to be an effective adjuvant and enhance the production of high titers of neutralizing antibodies against parvovirus B19 (Ballou et al. JID, 187:675-678 (2003)).

Mineral-Containing Compositions

Mineral containing compositions suitable for use as adjuvants in the invention include mineral salts, such as aluminum salts and calcium salts. The invention includes mineral salts such as hydroxides (e.g., oxyhydroxides), phosphates (e.g., hydroxyphosphates, orthophosphates), sulphates, etc. [e.g., see chapters 8 & 9 of *Vaccine Design* . . . (1995) eds. Powell & Newman. ISBN: 030644867X. Plenum.], or mixtures of different mineral compounds, with the compounds taking any suitable form (e.g., gel, crystalline, amorphous, etc.), and with adsorption being preferred. The mineral containing compositions may also be formulated as a particle of metal salt.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy, in particular by the presence of an adsorption band at 1070 $cm^{-1}$ and a strong shoulder at 3090-3100 $cm^{-1}$ [chapter 9 of *Vaccine Design* . . . (1995) eds. Powell & Newman. ISBN: 030644867X. Plenum.] The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g., as seen in transmission electron micrographs) is typical for aluminum hydroxide adjuvants. The pI of aluminum hydroxide adjuvants is typically about 11, i.e., the adjuvant itself has a positive surface charge at physiological pH. Adsorptive capacities of between 1.8-2.6 mg protein per mg $Al^{3+}$ at pH 7.4 have been reported for aluminum hydroxide adjuvants.

The adjuvants known as "aluminum phosphate" are typically aluminum hydroxyphosphates, often also containing a small amount of sulfate (i.e., aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. For example, an IR spectrum band at 3164 $cm^{-1}$ (e.g., when heated to 200° C.) indicates the presence of structural hydroxyls [ch. 9 of *Vaccine Design* . . . (1995) eds. Powell & Newman. ISBN: 030644867X. Plenum.].

The $PO_4/Al^{3+}$ molar ratio of an aluminum phosphate adjuvant will generally be between 0.3 and 1.2, preferably between 0.8 and 1.2, and more preferably 0.95+0.1. The aluminum phosphate will generally be amorphous, particularly for hydroxyphosphate salts. A typical adjuvant is amorphous aluminum hydroxyphosphate with $PO_4/Al$ molar ratio between 0.84 and 0.92, included at 0.6 mg $Al^{3+}$/ml. The aluminum phosphate will generally be particulate (e.g., plate-like morphology as seen in transmission electron micrographs). Typical diameters of the particles are in the range 0.5-20 µm (e.g., about 5-10 µm) after any antigen adsorption. Adsorptive capacities of between 0.7-1.5 mg protein per mg $Al^{3+}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5, e.g., about 5.7.

Suspensions of aluminum salts used to prepare compositions of the invention may contain a buffer (e.g., a phosphate or a histidine or a Tris buffer), but this is not always necessary. The suspensions are preferably sterile and pyrogen-free. A suspension may include free aqueous phosphate ions, e.g., present at a concentration between 1.0 and 20 mM, preferably between 5 and 15 mM, and more preferably about 10 mM. The suspensions may also comprise sodium chloride.

In one embodiment, an adjuvant component includes a mixture of both an aluminum hydroxide and an aluminum phosphate. In this case there may be more aluminum phosphate than hydroxide, e.g., a weight ratio of at least 2:1, e.g., >5:1, >6:1, >7:1, >8:1, >9:1, etc.

The concentration of $Al^{3+}$ in a composition for administration to a patient is preferably less than 10 mg/ml, e.g., <5 mg/ml, <4 mg/ml, <3 mg/ml, <2 mg/ml, <1 mg/ml, etc. A preferred range is between 0.3 and 1 mg/ml. A maximum of <0.85 mg/dose is preferred.

Oil Emulsions

Oil emulsion compositions suitable for use as adjuvants in the invention include squalene-water emulsions, such as MF59™ [Chapter 10 of *Vaccine Design* . . . (1995) eds. Powell & Newman. ISBN: 030644867X. Plenum.] (5% Squalene, 0.5% TWEEN 80™, and 0.5% SPAN 85™, formulated into submicron particles using a microfluidizer). Complete Freund's adjuvant (CFA) and incomplete Freund's adjuvant (IFA) may also be used.

Various suitable oil-in-water emulsions are known, and they typically include at least one oil and at least one surfactant, with the oil(s) and surfactant(s) being biodegradable (metabolizable) and biocompatible. The oil droplets in the emulsion are generally less than 5 μm in diameter, and advantageously the emulsion comprises oil droplets with a sub-micron diameter, with these small sizes being achieved with a microfluidizer to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl 2,6,10,14,18,22-tetracosahexaene. Other preferred oils are the tocopherols (see below). Oil in water emulsions comprising squalene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as theTWEENs™), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl)groups, with octoxynol-9 (TRITON X-100™, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs™), such as sorbitan trioleate (SPAN 85™) and sorbitan monolaurate. Preferred surfactants for including in the emulsion are TWEEN 80™ (polyoxyethylene sorbitan monooleate), SPAN 85™ (sorbitan trioleate), lecithin and TRITON X-100™. As mentioned above, detergents such as TWEEN 80™ may contribute to the thermal stability seen in the examples below.

Mixtures of surfactants can be used, e.g., TWEEN 80™/SPAN 85™ mixtures. A combination of a polyoxyethylene sorbitan ester such as polyoxyethylene sorbitan monooleate (TWEEN 80™) and an octoxynol such as t-octylphenoxypolyethoxyethanol (TRITON X-100™) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80™) 0.01 to 1%, in particular about 0.1%; octyl- or nonylphenoxy polyoxyethanols (such as TRITON X100™, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, TWEEN 80™, and SPAN 85™. The composition of the emulsion by volume can be about 5% squalene, about 0.5% polysorbate 80 and about 0.5% SPAN 85™. In weight terms, these ratios become 4.3% squalene, 0.5% polysorbate 80 and 0.48% SPAN 85™. This adjuvant is known as 'MF59™'. The MF59™ emulsion advantageously includes citrate ions, e.g., 10 mM sodium citrate buffer.

An emulsion comprising squalene, an α-tocopherol, and polysorbate 80. These emulsions may have from 2 to 10% squalene, from 2 to 10% tocopherol and from 0.3 to 3% TWEEN 80™, and the weight ratio of squalene:tocopherol is preferably <1 (e.g., 0.90) as this provides a more stable emulsion. Squalene and TWEEN 80™ may be present volume ratio of about 5:2, or at a weight ratio of about 11:5. One such emulsion can be made by dissolving TWEEN 80™ in PBS to give a 2% solution, then mixing 90 ml of this solution with a mixture of (5 g of DL-α-tocopherol and 5 ml squalene), then microfluidizing the mixture. The resulting emulsion may have submicron oil droplets, e.g., with an average diameter of between 100 and 250 nm, preferably about 180 nm.

An emulsion of squalene, a tocopherol, and a Triton detergent (e.g., TRITON X-100™). The emulsion may also include a 3d-MPL (see below). The emulsion may contain a phosphate buffer.

An emulsion comprising a polysorbate (e.g., polysorbate 80), a Triton detergent (e.g., TRITON X100™) and a tocopherol (e.g., an α-tocopherol succinate). The emulsion may include these three components at a mass ratio of about 75:11:10 (e.g., 750 μg/ml polysorbate 80, 110 μg/ml TRITON X-100™ and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("PLURONIC L121™"). The emulsion can be formulated in phosphate buffered saline, pH 7.4. This emulsion is a useful delivery vehicle for muramyl dipeptides, and has been used with threonyl-MDP in the "SAF-1" adjuvant (0.05-1% Thr-MDP, 5% squalane, 2.5% PLURONIC L121™ and 0.2% polysorbate 80). It can also be used without the Thr-MDP, as in the "AF" adjuvant (5% squalane, 1.25% PLURONIC L121™ and 0.2% polysorbate 80). Microfluidization is preferred.

An emulsion comprising squalene, an aqueous solvent, a polyoxyethylene alkyl ether hydrophilic nonionic surfactant (e.g., polyoxyethylene (12) cetostearyl ether) and a hydrophobic nonionic surfactant (e.g., a sorbitan ester or mannide ester, such as sorbitan monoleate or 'SPAN 80™'). The emulsion is preferably thermoreversible and/or has at least 90% of the oil droplets (by volume) with a size less than 200 nm. The emulsion may also include one or more of: alditol; a cryoprotective agent (e.g., a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. Preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, TWEEN 80™ or SPAN 80™). Additives may be included, such as QuilA saponin, cholesterol, a saponin-lipophile conjugate (such as GPI-0100, produced by addition of aliphatic amine to desacylsaponin via the carboxyl group of glucuronic acid), dimethyidioctadecylammonium bromide and/or N,Ndioctadecyl-N,N-bis(2-hydroxyethyl) propanediamine.

An emulsion comprising a mineral oil, a non-ionic lipophilic ethoxylated fatty alcohol, and a non-ionic hydrophilic surfactant (e.g., an ethoxylated fatty alcohol and/or polyoxyethylene-polyoxypropylene block copolymer) (see WO2006/113373).

An emulsion comprising a mineral oil, a non-ionic hydrophilic ethoxylated fatty alcohol, and a non-ionic lipophilic surfactant (e.g., an ethoxylated fatty alcohol and/or polyoxyethylene-polyoxypropylene block copolymer) (see WO2006/113373).

An emulsion in which a saponin (e.g., QuilA or QS21) and a sterol (e.g., a cholesterol) are associated as helical micelles.

Antigens and adjuvants in a composition will typically be in admixture at the time of delivery to a patient. The emulsions may be mixed with antigen during manufacture, or extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g., between 5:1 and 1:5) but is generally about 1:1. Saponin formulations (see chapter 22 of *Vaccine Design* . . . (1995) eds. Powell & Newman. ISBN: 030644867X. Plenum.)

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree has been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol.

Combinations of saponins and cholesterols can be used to form unique particles called immunostimulating complexes (ISCOMs) (chapter 23 of *Vaccine Design* . . . (1995) eds. Powell & Newman. ISBN: 030644867X. Plenum.). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in WO96/33739. Optionally, the ISCOMS may be devoid of additional detergent.

Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr phage, AP205 phage, and Ty (such as retrotransposon Ty protein p1).

Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in EP-A-0689454. Such "small particles" of 3dMPL are small enough to be sterile filtered through a 0.22 μm membrane (EP-A-0689454). Other nontoxic LPS derivatives include monophosphoryl lipid A mimics, such as aminoalkyl glucosaminide phosphate derivatives, e.g., RC-529.

Lipid A derivatives include derivatives of lipid A from *Escherichia coli* such as OM-174. OM-174 is described for example in Meraldi et al. (2003) *Vaccine* 21:2485-2491 and Pajak et al. (2003) *Vaccine* 21:836-842.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References Kandimalla et al. (2003) *Nucleic Acids Research* 31:2393-2400; WO02/26757, and WO99/62923 disclose possible analog substitutions, e.g., replacement of guanosine with 2'-deoxy-7-deazaguanosine. The adjuvant effect of CpG oligonucleotides is further discussed in Krieg (2003) Nature Medicine 9:831-835; McCluskie et al. (2002) FEMS Immunology and Medical Microbiology 32:179-185; WO98/40100; U.S. Pat. No. 6,207,646; U.S. Pat. No. 6,239,116; and U.S. Pat. No. 6,429,199.

The CpG sequence may be directed to TLR9, such as the motif GTCGTT (SEQ ID NO: 11) or TTCGTT (SEQ ID NO: 12) (Kandimalla et al. (2003) *Biochemical Society Transactions* 31 (part 3):654- 658). The CpG sequence may be specific for eliciting a Th1 immune response, such as a CpG-A ODN, or it may be more specific for eliciting a B cell response, such a CpG-B ODN. CpG-A and CpG-B ODNs are discussed in Blackwell et al. (2003) J Immunol 170: 4061-4068; Krieg (2002) Trends Immunol 23:64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *Biochemical Society Transactions* 31 (part 3):654-658 & Kandimalla et al. (2003) BBRC 306: 948-953; Bhagat et al. (2003) BBRC 300:853-861 and WO03/035836

A particularly useful adjuvant based around immunostimulatory oligonucleotides is known as IC-31™ (Schellack et al. (2006) *Vaccine* 24:5461-72). Thus an adjuvant used with the invention may comprise a mixture of (i) an oligonucleotide (e.g., between 15-40 nucleotides) including at least one (and preferably multiple) CpI motifs (i.e., a cytosine linked to an inosine to form a dinucleotide), and (ii) a polycationic polymer, such as an oligopeptide (e.g., between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 2). The polycationic polymer may be a peptide comprising 11-mer amino acid sequence KLKLLLLLKLK (SEQ ID NO: 3).

Bacterial ADP-ribosylating toxins and detoxified derivatives thereof maybe used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in Beignon et al. (2002) Infect Immun 70:3012-3019; Pizza et al. (2001) Vaccine 19:2534-2541; Pizza et al. (2000) Int J Med Microbiol 290:455-461; Scharton-Kersten et al. (2000) Infect Immun 68:5306-5313; Ryan et al. (1999) Infect Immun 67:6270-6280; Partidos et al. (1999) Immunol Lett 67:209-216; Peppoloni et al. (2003) Expert Rev Vaccines 2:285-293; Pine et al. (2002) J Control Release 85:263-270 and Tebbey et al. (2000) Vaccine 18:2723-34. A useful CT mutant is or CT-E29H. Numerical reference for amino acid substitutions is preferably based on the alignments of the A and B subunits of ADP-ribosylating toxins set forth in Domenighini et al. (1995) *Mol Microbiol* 15:1165-1167, specifically incorporated herein by reference in its entirety.

Human Immunomodulators

Human immunomodulators suitable for use as adjuvants in the invention include cytokines, such as interleukins (e.g., IL-1, IL-2, IL-4, IL-5, IL-6, IL-7, IL-12, etc.) (WO99/40936 and WO99/44636), interferons (e.g., interferon-γ), macrophage colony stimulating factor, and tumor necrosis factor. A preferred immunomodulator is IL-12.

Bioadhesives and Mucoadhesives

Bioadhesives and mucoadhesives may also be used as adjuvants in the invention. Suitable bioadhesives include esterified hyaluronic acid microspheres (Singh et al] (2001) *J Cont Release* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO99/27960).

Microparticles

Microparticles may also be used as adjuvants in the invention. Microparticles (i.e., a particle of ~100 nm to ~150 mm in diameter, more preferably ~200 nm to ~30 μm in diameter, and most preferably ~500 nm to ~10 μm in diameter) formed from materials that are biodegradable and non-toxic (e.g., a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g., with SDS) or a positively-charged surface (e.g., with a cationic detergent, such as CTAB).

Liposomes (Chapters 13 & 14 of *Vaccine Design* . . . (1995) eds. Powell & Newman. ISBN: 030644867X. Plenum.)

Examples of liposome formulations suitable for use as adjuvants are described in U.S. Pat. Nos. 6,090,406, 5,916, 588 and EP A 0626169.

Polyoxyethylene Ether and Polyoxyethylene Ester Formulations

Adjuvants suitable for use in the invention include polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Polyphosphazene (PCPP)

PCPP formulations are described, for example, in Andrianov et al. (1998) Biomaterials 19:109-115 and Payne et al. (1998) *Adv Drug Delivery Review* 31:185-196.

Muramyl Peptides

Examples of muramyl peptides suitable for use as adjuvants in the invention include N-acetyl-muramyl-L-threonyl-D-isoglutamine (thr-MDP), N-acetylnormuramyl-L-alanyl-D-isoglutamine (nor-MDP), and N-acetylmuramyl-L-alanyl-Disoglutaminyl-L-alanine-2-(1'-2'-dipalmitoyl-sn-glycero-3-hydroxyphosphoryloxy)-ethylamine MTP-PE).

Imidazoquinolone Compounds

Examples of imidazoquinolone compounds suitable for use adjuvants in the invention include Imiquamod and its homologues (e.g., "Resiquimod 3M"), described further in Stanley (2002) *Clin Exp Dermatol* 27:571-577 and Jones (2003) *Curr Opin Investig Drugs* 4:214-218.

The invention may also include combinations of aspects of one or more of the adjuvants identified above. For example, the following adjuvant compositions may be used in the invention: (1) a saponin and an oil-in-water emulsion (WO99/11241); (2) a saponin (e.g., QS21)+a non-toxic LPS derivative (e.g., 3dMPL) (WO94/00153); (3) a saponin (e.g., QS21)+a non-toxic LPS derivative (e.g., 3dMPL)+a cholesterol; (4) a saponin (e.g., QS21)+3dMPL+IL-12 (optionally+a sterol) (WO98/57659); (5) combinations of 3dMPL with, for example, QS21 and/or oil-in-water emulsions (European patent applications 0835318, 0735898 and 0761231); (6) SAF, containing 10% squalane, 0.4% TWEEN 80™, 5% pluronic-block polymer L121, and thr-MDP, either microfluidized into a submicron emulsion or vortexed to generate a larger particle size emulsion; (7) RIBI™ adjuvant system (RAS), (Ribi Immunochem) containing 2% squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of *Vaccine Design . . .* (1995) eds. Powell & Newman. ISBN: 030644867X. Plenum. The use of an aluminum hydroxide and/or aluminum phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG and alum or resiquimod and alum. A combination of aluminum phosphate and 3dMPL may be used.

Vaccines and Methods of Raising Immune Response

Immunogenic compositions may be useful as vaccines. Vaccines according to the invention may either be prophylactic (i.e., to prevent infection) or therapeutic (i.e., to treat infection), but will typically be prophylactic. Immunogenic compositions used as vaccines contain an immunologically effective amount of antigen(s), as well as any other components, as needed. By immunologically effective amount, it is meant that the administration of that amount to a subject, either in a single dose or as part of a series, is effective for treatment or prevention. This amount varies depending upon the health and physical condition of the subject to be treated, age, the taxonomic group of individual to be treated (e.g., non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The invention also provides a delivery device pre-filled with an immunogenic composition described herein.

The immunogenic compositions, polynucleotides, and vaccines described herein can be used in methods to raise an immune response in a subject for protection against parvovirus infection. The subjects are vertebrates, preferably a human, but may also be mouse, Aleutian mink, cow, canine, duck, monkey, chimpanzee, gorilla, orangutan, bonobo, or other primate. Preferred human subjects include individuals suffering from sickle cell anemia or any blood dyscrasia, transplant patients, female individuals of child-bearing age, in particular pregnant females, and individuals who plan to undergo a medical procedure causing immunosuppression.

Due to similarity between the VP1 unique regions of the different parvoviruses, in some cases, the administered composition contains a mutant polypeptide VP1 unique region polypeptide from a certain parvovirus genus, species, or strain capable of infecting a certain vertebrate, but the immunogenic composition or vaccine is capable of raising an immune response in a different vertebrate to either the same or different parvovirus genus, species, or strain. Protection against parvovirus infection may provide protection against certain diseases including, but not limited to fifth disease, hydrops fetalis, and aplastic crisis.

The immunogenic compositions and vaccines described above include polypeptide antigens. In all cases, however, the polypeptide antigens can be replaced by polynucleotides (typically DNA) encoding those polypeptides, to give compositions, vaccines, methods and uses based on nucleic acid immunization. The nucleic acid encoding the immunogen is expressed in vivo after delivery and the expressed immunogen then stimulates the immune system. Nucleic acid immunization is now a developed field.

The invention also provides a method for eliciting parvovirus neutralizing antibodies by administering an effective amount of an immunogenic composition, polynucleotide, or vaccine.

V. Methods and Kits for Use of Mutant Parvovirus VP1 Unique Region Polypeptides

The correlation demonstrated herein between antibody binding to the described mutant parvovirus VP1 unique region polypeptides and parvovirus neutralization ability makes these polypeptides useful for any method that requires the ability to selectively estimate neutralizing antibody titer.

Assessing Immunogenicity of Parvovirus Vaccine Components

In certain embodiments, the invention relates to methods for assessing the functional immunogenicity of a parvovirus vaccine component by providing an antibody preparation from a subject inoculated with a parvovirus vaccine component by contacting the antibody preparation with a mutant VP1 unique region polypeptide described herein and assessing functional immunogenicity of a parvovirus vaccine component by detecting whether the antibody preparation binds to the polypeptide.

Suitable vaccines that may be assayed using the methods and compositions disclosed herein include any material that raises a humoral immune response to parvovirus. Suitable vaccines assayed can include antigens in the context of live, attenuated, or inactivated parvovirus. The components of the vaccine can be a protein, a proteoglycan, a lipoprotein, an outer membrane vesicle, a virus-like particle, or an entire vaccine. Typically, the vaccine to be assayed includes VP1 unique region as a component, and in some embodiments, the mutant VP1 unique region polypeptides described herein.

For vaccines comprising polynucleotides that express antigens, one of skill in the art would recognize that the antibody preparation to be used to assess functional immunogenicity binds the encoded antigen rather than the polynucleotide.

The methods and compositions disclosed herein can be used to determine functional immunogenicity of vaccines for any use, including but not limited to, clinical trials, to assess manufacture of a vaccine to verify that each batch manufactured demonstrates requisite functional immunogenicity, to assess functional immunogenicity after administration to specific subjects, and to assess functional immunogenicity against a particular strain of parvovirus using a mutant parvovirus VP1 unique region from that strain.

Other Methods

In some embodiments, the invention relates to methods of identifying subjects who may be at risk for parvovirus infection by providing an antibody preparation from a subject who may be at risk for parvovirus infection; contacting the antibody preparation with a mutant VP1 unique region polypeptide described herein; and identifying subjects who may be at risk for parvovirus infection by detecting whether the antibody preparation binds to the polypeptide. Typically, the subject may be at risk for infection because the subject may have been exposed to parvovirus or may have been in an environment likely to contain parvovirus, such as those with a large number of children.

In other embodiments, the invention relates to methods for determining whether an antibody preparation is likely to contain neutralizing parvovirus antibodies by providing an antibody preparation; contacting the antibody preparation with a mutant VP1 unique region polypeptide described herein; and determining whether an antibody preparation is likely to contain neutralizing parvovirus antibodies by detecting whether the antibody preparation binds to the isolated polypeptide. The invention may be used to determine the potency of the antibody preparation.

The mutant VP1 unique region polypeptides described herein can be used in methods as a general diagnostic for blood products. The antibody preparation to be tested may be immune globulins (IV-IG), which is used as a therapy for parvovirus B19 infection. Alternatively, the antibody preparation is from a subject who has been exposed to parvovirus, treated for parvovirus infection, or vaccinated against parvovirus.

In still other embodiments, the invention relates to methods of measuring a correlate of efficacy to assess treatment for parvovirus infection by providing an antibody preparation from a subject having received the treatment for parvovirus infection; contacting the antibody preparation with a mutant VP1 unique region polypeptide described herein; and measuring a correlate of efficacy to assess treatment for parvovirus infection by detecting whether the antibody preparation binds to the isolated polypeptide. Typically, the treatment for parvovirus infection to be assessed is administration of immune globulins.

Antibody Preparations

The antibody preparations used in the methods disclosed herein may be obtained from any source so long as the binding of the antibody to the mutant parvovirus VP1 unique region polypeptides described herein can be correlated to its neutralization ability. In certain embodiments, the antibody preparation may be in the form of an antibody containing serum sample, polyclonal antibodies, antigen-purified polyclonal antibodies or monoclonal antibodies.

In embodiments where the antibody preparation is to be used to assess functional immunogenicity of a parvovirus vaccine component, to identify subjects who may be at risk for parvovirus infection, or to measure a correlate of efficacy to assess treatment for parvovirus infection, a sample is taken, respectively from a subject who is inoculated with the vaccine, who may be at risk for infection, or who has received a treatment.

In other embodiments the antibody preparation itself is a treatment for parvovirus infection, such as immune globulins, which is assayed prior to administration in order determine whether neutralizing antibodies are present, the titer of the antibodies present, and the potency of the preparation.

Assays for Detection of Binding

In order to practice the methods described herein, the ability of an antibody preparation to bind the mutant VP1 unique region polypeptide is detected using any technique available to one of skill in the art for detection of antibody binding. By way of example, detection methods include Western blot, ELISA, lateral flow assay, latex agglutination, immunochromatographic strips, fluorescence (including multichannel flow cytometric fluorescence detection methods), rate nephelometry, and immunoprecipitation.

In certain embodiments, the mutant parvovirus VP1 unique region polypeptide may be fixed to a solid support such as a multi-well plate such as a 96 or 384-well plate, bead, sphere, membrane, colloidal metal (e.g., gold), porous member, surfaces of capillary (e.g., in flow through test), test strip or latex particle. The mutant parvovirus VP1 unique region polypeptide may be affixed to such a solid support either directly or by indirect linkage such as a capture antibody as used in sandwich ELISA. Examples of direct linkages to a support include covalent binding, non-covalent binding, or adsorption to a surface of the support or within the support in the case of a gel support such as agarose or acrylamide.

When using ELISA-based detection, any suitable assayable enzyme may be used including by way of example, horse-radish peroxidase, alkaline phosphatase, β-galactosidase, luciferase, and acetylcholinesterase. One of skill in the art may select any suitable substrate for the enzyme chosen such as a chromogenic, radiolabeled or a fluorescent substrate.

When practicing the methods described herein, the assessment to be achieved by the method may be determined by any suitable method for analyses of the results of the particular antibody binding assay that may be correlated to the parameter to be measured. In an exemplary embodiment relating to a method of assessing functional immunogenicity of a parvovirus vaccine component, the assay may produce a binary result such as a latex agglutination assay which is tuned such that no aggregation occurs when a vaccine is not functionally immunogenic against a pathogen while aggregation occurs when the vaccine is functionally immunogenic. In other embodiments, the analysis will produce a numerical value whereby a value above or below a threshold indicates functional immunogenicity. Preferred analysis methods with numerical output include the % $B_{max}$ method, and the signal-to-noise ratio (S/N) in which the signal from the pathogen sample is divided by the signal from the blank. For methods with numerical output a preferred embodiment would include a standard curve obtained with different concentrations of a reference antibody preparations and testing of several different dilutions of the mutant parvovirus VP1 unique region polypeptide.

Kits

The methods and compositions disclosed herein may be embodied in a kit for the practice of the assays. In one aspect, the kits for use in methods and compositions as disclosed herein will include mutant parvovirus VP1 unique region polypeptide linked to a detection moiety.

VI. General

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism as long as the polypeptide or polynucleotide is distinguishable from the endogenous polypeptide or polynucleotide in the organism, which organism may be living or non-living.

The term "comprising" encompasses "including" as well as "consisting," e.g., a composition "comprising" X may consist exclusively of X or may include something additional, e.g., X+Y.

The term "about" in relation to a numerical value x means, for example, x±10%.

VII. Examples

This example illustrates that measurement of antibody binding to a mutant parvovirus VP1 unique region polypeptide having a mutated epitope for non-neutralizing antibodies can be used to determine whether an antibody preparation is likely to contain parvovirus-neutralizing antibodies.

To evaluate whether the VP1 unique region can be used to determine whether an antibody preparation is likely to contain parvovirus-neutralizing antibodies, a B19 VP1 unique region polypeptide based upon the wildtype sequence ("VP1u wt") was generated. The polypeptide was tested in an ELISA for binding to sera from mouse inoculated with parvovirus B19 VLPs (made of VP1 and VP2 together). Sera previously shown to contain neutralizing antibodies by a cell-based neutralization assay had a high ELISA titer, and most sera lacking neutralizing antibody did not have a high ELISA titer. However, some binding to VP1u wt was observed for non-neutralizing sera as well.

Thus, there was no clear correlation between sera binding to the full VP1 unique region polypeptide and the ability of the sera to neutralize parvovirus.

The non-neutralizing sera which bound to VP1u wt was obtained from mice inoculated with VLPs containing VP2 alone which had therefore never been exposed to the VP1u wt sequence. This led the inventors to hypothesize that the VP1 unique region contained a VP2 epitope. To test this hypothesis, MAB8293 (Millipore), a monoclonal antibody with a known VP2 epitope of PYHHW (SEQ ID NO: 8), was tested by ELISA for binding to VP1u wt. MAB8293 bound to VP1u wt, confirming that the VP1 unique region contained a VP2 epitope. Sequence analysis showed the region of similarity between the VP1u region extending from amino acid 167 to amino acid 171 of parvovirus B19 VP1 (PYTHW (SEQ ID NO: 7)) and the VP2 epitope (PYHHW (SEQ ID NO:8)) (FIG. 1).

Two mutant proteins removing this region of similarity, an AATAA (SEQ ID NO: 9) mutant and a more conservative AYTAA (SEQ ID NO: 10) mutant (FIG. 2), were tested by ELISA to confirm that the VP2 monoclonal antibody MAB8294 no longer bound. Results showed that either mutation knocked out binding of MAB8294 in the ELISA (FIG. 3, Table 1).

Mouse sera that reacted with VP1u wt but lacked neutralization activity as measured by a cell-based neutralization assay (VP2 alone +MF59™ 5 µg dose and Parvo VLPs 0.05 µg dose) were tested in an ELISA with the mutant VP1u proteins (AATAA (SEQ ID NO: 9) and AYTAA (SEQ ID NO: 10)). The non-neutralizing mouse sera did not react with the mutant VP1u protein but still reacted with the VP1u wt protein (FIG. 3). This confirmed that some antibodies could be raised to the wildtype epitope (either in the context of VP2 or the VP1u) but are non-neutralizing.

Table 1 is a table of ELISA results for the different VP1u constructs. Group 4 is the 5wp3 time point from the 0.05 µg mutVP1NP2/MF59™ dose; Group 6 is the 5wp3 time point from the 5.0 µg mutVP1NP2/MF59™ dose; Group 12 is the 5wp3 time point from the 5.0 µg VP2/MF59™ dose; mAb is the monoclonal antibody MAB8293 (Millipore). "Nt" signifies not tested and the 5wp3 time point refers to 5 weeks post-3rd immunization. For this series of experiments the mutVP1 stands for a distinct mutation from any discussed above that abrogate the $PLA_2$ activity of VP1.

| | | | | IgG Titer[a] | | | |
|---|---|---|---|---|---|---|---|
| | Vaccine | | | | | VP1u | VP1u | Neutral- |
| Sample | Antigen | Dose (mg) | Adjuvant | VP1u WT | AT mut | YT mut | ization Activity |
| mAb | | | | 4670 | <25 | <25 | nt[b] |
| Gr. 4 pool | Mut VP1/VP2 | 0.05 | MF59 ™ | 1360 | <25 | <25 | no |
| Gr. 6 pool | Mut VP1/VP2 | 5 | MF59 ™ | 4760 | 2760 | 1350 | yes |
| Gr. 12 pool | VP2 | 5 | MF59 ™ | 2360 | <25 | <25 | no |

FIG. 5 shows the ELISA titers of samples from the three groups shown in table 1 as well as a fourth group (group 5) taken at 21 days, 42 days, 56 days, 77 days and 119 days. The samples taken at 56 and 77 days were also assayed for their neutralization potential. The sera samples from groups 4 and 12 were negative in the neutralization assay for both time points. The sera samples from groups 5 and 6 were positive in the neutralization assay. As can be seen in FIG.

5(B), the ELISA titers using the mutant (AT) VP1u show a strong correlation with the neutralization capacity of the sera and therefore the ability of the VP1u mutants to be used in assessing functional immunogenicity of a vaccine candidate or immunogenic composition. By contrast, as can be seen in FIG. 5(A), the ELISA titers using the wild-type VP1u shows little correlation since all four groups produce an IgG response within an order of magnitude at each time point despite two of the four groups being seronegative as measured by the neutralization assay.

Table 2 is an additional table of ELISA results for the different VP1u constructs. As above, for this series of experiments the mutVP1 stands for a distinct mutation from any discussed above that abrogate the $PLA_2$ activity of VP1. FIG. 6 shows the percent neutralization of the serial dilutions of the seven groups shown in Table 2 below. Table 2 and FIG. 6 confirm that the ELISA assay using the VP1u construct can differentiate between seropositive and seronegative results. Furthermore, as can be seen with seropositive group 5, the ELISA assay can differentiate between a strong neutralizing response and weak neutralizing responses.

| ELISA Results | Group Number (seropositive or seronegative) | | | | | | |
|---|---|---|---|---|---|---|---|
| | 1 (−) | 2 (−) | 1 (+) | 2 (+) | 3 (+) | 4 (+) | 5 (+) |
| VP1u (wt) | − | − | +++ | +++ | +++ | +++ | + |
| VP1u (mt) | − | − | +++ | +++ | +++ | +++ | + |

Materials and Methods

The parvovirus B19 cell based neutralization assay employed is a qRT-PCR based assay that uses live parvovirus B19 (genotype 1) as the input and erythroid progenitor cells as the substrate. Briefly, erythroid progenitor cells are differentiated from human peripheral blood monocytes as described in the literature (Filippone, C. *PLoS One.* 5:e9496 (2010)). These cells were either infected with virus or virus that had been previously incubated with sera for one hour at 4° C. After incubation at 37° C. for 48 hours, RNA was extracted and qRT-PCR was performed with primers directed to a splice variant that is only present in infected cells and not the original input virus.

VP1 unique region constructs were generated with C-terminal 6×His tags to enable quick purification. In short, expression plasmids were designed to inducibly express the VP1 unique region in *E. coli* cells. After expression, cells were broken open with sonication and cell supernatant was applied to a nickel column. Due to high expression levels, a single step of purification leads to >90% pure protein which can be dialyzed into a final buffer for storage at 4° C.

The VP1 unique region construct ELISA was made using standard techniques. 96-well flat-bottom plates ("ELISA plates") was coated with the relevant protein construct. Following a blocking step, diluted serum samples from different studies was applied to the plate along with a standard. After incubation for an optimized time, a detection antibody was added and followed by an appropriate substrate. The plates were then measured at OD450 and data was interpreted.

SEQUENCES

SEQ ID NO: 1
Parvovirus B19 VP1 unique region
MSKKSGKWWESDDKFAKAVYQQFVEFYEKVTGTDLELIQILKDHYNISLDNPLENPSSLF

DLVARIKNNLKNSPDLYSHHFQSHGQLSDHPHALSSSSSHAEPRGENAVLSSEDLHKPGQ

VSVQLPGTNYVGPGNELQAGPPQSAVDSAARIHDFRYSQLAKLGINPYTHWTVADEELLK

NIKNETGFQAQVVKDYFTLKGAAAPVAHFQGSLPEVPAYNASEKYPS

SEQ ID NO: 2: Deoxyribonucleotide
5'-(IC)$_{13}$-3'

SEQ ID NO: 3: Amino acid sequence
KLKLLLLLKLK

SEQ ID NO: 4
Parvovirus B19 VP1 unique region (Type 1)
MSKESGKWWESDDKFAKAVYQQLVEFYEKVTGTDLELIQILKDHYNISLDNPLENPSSLF        60

DLVARIKNNLKNSPDLYSHHFQSHGQLSDHPHALSSSSSHAEPRGENAVLSSEDLHKPGQ       120

VSVQLPGTNYVGPGNELQAGPPQSAVDSAARIHDFRYSQLAKLGINPYTHWTVADEELLK       180

NIKNETGFQAQVVKDYFTLKGAAAPVAHFQGSLPEVPAYNASEKYPS                    227

SEQ ID NO: 5
Parvovirus B19 VP1 unique region (Type 2)
MSKESGKWWESDDKFAKDVYKQFVEFYEKVTGTDLELIQILKDHYNISLDNPLENPSSLF        60

DLVARIKSNLKDSPDLYSHHFQSHGQLSDHPHALSPSSSHTEPRGENAVLSSEDLHKPGQ       120

VSIQLPGTNYVGPGYELQAGPPQSAVDSAARIHDFRYSQLAKLGINPYTYWTVADEELLK       180

NIKNESGFQAQAVKDYFTLKGAAAPVAHFQGSLPEVPAYNASEKYPS                    227

SEQ ID NO: 6
Parvovirus B19 VP1 unique region (Type 3)
MSKTTDKWWESSDKFAQDVYKQFVQFYEKATGTDLELIQILKDHYNISLDNPLENPSSLF        60

```
DLVARIKSNLKNSPDLYSHHFQSHGQLSDHPHALSPSNSSTEPRGENAVLSSEDLHKPGQ        120

VSIQLPGTNYVGPGNELQAGPPQNAVDSAARIHDFRYSQLAKLGINPYTHWTVADEELLK        180

NIKNETGFQAQAVKDYFTLKGAAAPVAHFQGSLPEVPAYNASEKYPS                     227
```

What is claimed is:

1. A polypeptide comprising a parvovirus VP1 unique region selected from SEQ ID NO: 1, SEQ ID NO: 4, SEQ ID NO:5 and SEQ ID NO:6, wherein the sequence of amino acids at positions 167-171 of said parvovirus unique region has at least two amino acid mutations, where each of said mutations is an amino acid substitution or an amino acid deletion, and wherein the parvovirus VP1 unique region does not cross-react with antibodies that bind parvovirus VP2.

2. An immunogenic composition comprising the polypeptide of claim 1 and a pharmaceutically acceptable carrier.

3. A method of raising an immune response to parvovirus in a subject comprising administering the immunogenic composition of claim 2 to the subject.

4. The polypeptide of claim 1, wherein the sequence of amino acids corresponding to positions 167-171 of SEQ ID NO:1 has at least three amino acid substitutions or deletions.

5. The polypeptide of claim 1, wherein the sequence of amino acids corresponding to positions 167-171 of SEQ ID NO:1 has at least four amino acid substitutions or deletions.

6. The polypeptide of claim 1, which does not include a Y168F or H170Y substitution.

* * * * *

SEQUENCE LISTING

<160> NUMBER OF SEQ ID NOS: 12

<210> SEQ ID NO 1
<211> LENGTH: 227
<212> TYPE: PRT
<213> ORGANISM: Parvovirus B19

<400> SEQUENCE: 1

```
Met Ser Lys Lys Ser Gly Lys Trp Trp Glu Ser Asp Asp Lys Phe Ala
 1               5                  10                  15

Lys Ala Val Tyr Gln Gln Phe Val Glu Phe Tyr Glu Lys Val Thr Gly
            20                  25                  30

Thr Asp Leu Glu Leu Ile Gln Ile Leu Lys Asp His Tyr Asn Ile Ser
        35                  40                  45

Leu Asp Asn Pro Leu Glu Asn Pro Ser Ser Leu Phe Asp Leu Val Ala
    50                  55                  60

Arg Ile Lys Asn Asn Leu Lys Asn Ser Pro Asp Leu Tyr Ser His His
65                  70                  75                  80

Phe Gln Ser His Gly Gln Leu Ser Asp His Pro His Ala Leu Ser Ser
                85                  90                  95

Ser Ser Ser His Ala Glu Pro Arg Gly Glu Asn Ala Val Leu Ser Ser
            100                 105                 110

Glu Asp Leu His Lys Pro Gly Gln Val Ser Val Gln Leu Pro Gly Thr
        115                 120                 125

Asn Tyr Val Gly Pro Gly Asn Glu Leu Gln Ala Gly Pro Pro Gln Ser
    130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser
225
```

<210> SEQ ID NO 2
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 3, 5, 7, 9, 11, 13, 15, 17, 19, 21, 23, 25
<223> OTHER INFORMATION: n = inosine

<400> SEQUENCE: 2 ncncncnc ncncncnc ncncnc                                            26

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Lys Leu Lys Leu Leu Leu Leu Lys Leu Lys
1               5                   10

<210> SEQ ID NO 4
<211> LENGTH: 227
<212> TYPE: PRT
<213> ORGANISM: Parvovirus B19

<400> SEQUENCE: 4

Met Ser Lys Glu Ser Gly Lys Trp Trp Glu Ser Asp Asp Lys Phe Ala
1               5                   10                  15

Lys Ala Val Tyr Gln Gln Leu Val Glu Phe Tyr Glu Lys Val Thr Gly
                20                  25                  30

Thr Asp Leu Glu Leu Ile Gln Ile Leu Lys Asp His Tyr Asn Ile Ser
            35                  40                  45

Leu Asp Asn Pro Leu Glu Asn Pro Ser Ser Leu Phe Asp Leu Val Ala
50                  55                  60

Arg Ile Lys Asn Asn Leu Lys Asn Ser Pro Asp Leu Tyr Ser His His
65                  70                  75                  80

Phe Gln Ser His Gly Gln Leu Ser Asp His Pro His Ala Leu Ser Ser
                85                  90                  95

Ser Ser Ser His Ala Glu Pro Arg Gly Glu Asn Ala Val Leu Ser Ser
            100                 105                 110

Glu Asp Leu His Lys Pro Gly Gln Val Ser Val Gln Leu Pro Gly Thr
        115                 120                 125

Asn Tyr Val Gly Pro Gly Asn Glu Leu Gln Ala Gly Pro Pro Gln Ser
130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser
225

<210> SEQ ID NO 5
<211> LENGTH: 227
<212> TYPE: PRT
<213> ORGANISM: Parvovirus B19

<400> SEQUENCE: 5

Met Ser Lys Glu Ser Gly Lys Trp Trp Glu Ser Asp Asp Lys Phe Ala
1               5                   10                  15

Lys Asp Val Tyr Lys Gln Phe Val Glu Phe Tyr Glu Lys Val Thr Gly

Thr Asp Leu Glu Leu Ile Gln Ile Leu Lys Asp His Tyr Asn Ile Ser
            35                  40                  45

Leu Asp Asn Pro Leu Glu Asn Pro Ser Ser Leu Phe Asp Leu Val Ala
 50                  55                  60

Arg Ile Lys Ser Asn Leu Lys Asp Ser Pro Asp Leu Tyr Ser His His
 65                  70                  75                  80

Phe Gln Ser His Gly Gln Leu Ser Asp His Pro His Ala Leu Ser Pro
                85                  90                  95

Ser Ser Ser His Thr Glu Pro Arg Gly Glu Asn Ala Val Leu Ser Ser
            100                 105                 110

Glu Asp Leu His Lys Pro Gly Gln Val Ser Ile Gln Leu Pro Gly Thr
            115                 120                 125

Asn Tyr Val Gly Pro Gly Tyr Glu Leu Gln Ala Gly Pro Pro Gln Ser
            130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr Tyr Trp Thr Val Ala Asp Glu
                165                 170                 175

Glu Leu Leu Lys Asn Ile Lys Asn Glu Ser Gly Phe Gln Ala Gln Ala
            180                 185                 190

Val Lys Asp Tyr Phe Thr Leu Lys Gly Ala Ala Pro Val Ala His
            195                 200                 205

Phe Gln Gly Ser Leu Pro Glu Val Pro Ala Tyr Asn Ala Ser Glu Lys
210                 215                 220

Tyr Pro Ser
225

<210> SEQ ID NO 6
<211> LENGTH: 227
<212> TYPE: PRT
<213> ORGANISM: Parvovirus B19

<400> SEQUENCE: 6

Met Ser Lys Thr Thr Asp Lys Trp Trp Glu Ser Ser Asp Lys Phe Ala
 1               5                  10                  15

Gln Asp Val Tyr Lys Gln Phe Val Gln Phe Tyr Glu Lys Ala Thr Gly
                20                  25                  30

Thr Asp Leu Glu Leu Ile Gln Ile Leu Lys Asp His Tyr Asn Ile Ser
            35                  40                  45

Leu Asp Asn Pro Leu Glu Asn Pro Ser Ser Leu Phe Asp Leu Val Ala
 50                  55                  60

Arg Ile Lys Ser Asn Leu Lys Asn Ser Pro Asp Leu Tyr Ser His His
 65                  70                  75                  80

Phe Gln Ser His Gly Gln Leu Ser Asp His Pro His Ala Leu Ser Pro
                85                  90                  95

Ser Asn Ser Thr Glu Pro Arg Gly Glu Asn Ala Val Leu Ser Ser
            100                 105                 110

Glu Asp Leu His Lys Pro Gly Gln Val Ser Ile Gln Leu Pro Gly Thr
            115                 120                 125

Asn Tyr Val Gly Pro Gly Asn Glu Leu Gln Ala Gly Pro Pro Gln Asn
            130                 135                 140

Ala Val Asp Ser Ala Ala Arg Ile His Asp Phe Arg Tyr Ser Gln Leu
145                 150                 155                 160

```
Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Ala
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser
225

<210> SEQ ID NO 7
<211> LENGTH: 5
<212> TYPE: PRT
<213> ORGANISM: Parvovirus B19

<400> SEQUENCE: 7

Pro Tyr His His Trp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Pro Tyr Thr His Trp
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Ala Ala Thr Ala Ala
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Ala Tyr Thr Ala Ala
1               5

<210> SEQ ID NO 11
<211> LENGTH: 6
<212> TYPE: DNA
<213> ORGANISM: Artificial Sequence
<220> FEATURE:
<223> OTHER INFORMATION: Synthetic Construct

<400> SEQUENCE: 11 gtcgtt                                                                        6

<210> SEQ ID NO 12
```

```
<211> LENGTH: 6
<212> TYPE: DNA
<213> ORGANISM: Artificial Sequence
<220> FEATURE:
<223> OTHER INFORMATION: Synthetic Construct

<400> SEQUENCE: 12 ttcgtt                                                                        6
```